(12) United States Patent
Kim et al.

(10) Patent No.: US 9,798,137 B1
(45) Date of Patent: Oct. 24, 2017

(54) LASER OPERATION DEVICE CAPABLE OF STEERING THE LASER USING A LENS

(71) Applicant: KOREA INSTITUTE OF SCIENCE AND TECHNOLOGY, Seoul (KR)

(72) Inventors: Keri Kim, Seoul (KR); Seong Il Kwon, Seoul (KR); Heechul Kim, Atlanta, GA (US)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/362,067

(22) Filed: Nov. 28, 2016

(30) Foreign Application Priority Data

Oct. 27, 2016 (KR) .................... 10-2016-0141204

(51) Int. Cl.
*G02B 26/08* (2006.01)
*H01S 3/00* (2006.01)
*G02B 19/00* (2006.01)
*A61B 18/24* (2006.01)
*A61B 18/00* (2006.01)
*A61B 18/22* (2006.01)

(52) U.S. Cl.
CPC .......... *G02B 26/0875* (2013.01); *A61B 18/24* (2013.01); *G02B 19/0009* (2013.01); *G02B 19/0047* (2013.01); *H01S 3/0071* (2013.01); *A61B 2018/00339* (2013.01); *A61B 2018/2238* (2013.01); *A61B 2018/2266* (2013.01)

(58) Field of Classification Search
CPC ............ G02B 26/0875; G02B 19/0009; G02B 19/0047; G02B 7/08; G02B 7/09; G02B 7/04; A61B 18/24; A61B 2018/00339; A61B 2018/2238; A61B 2018/2266; H01S 3/0071
USPC ......... 359/196.1, 198.1, 209.1–210.2, 221.2; 600/160, 173, 178; 606/17
See application file for complete search history.

(56) References Cited

U.S. PATENT DOCUMENTS

| 5,242,439 A | 9/1993 | Larsen et al. |
| 2012/0265094 A1* | 10/2012 | Goldfarb .............. A61B 1/0014 600/562 |
| 2013/0041309 A1 | 2/2013 | Siegel |

FOREIGN PATENT DOCUMENTS

| EP | 2 540 247 B1 | 4/2016 |
| KR | 10-2009-0115727 A | 11/2009 |
| KR | 10-2016-0021959 A | 2/2016 |

* cited by examiner

*Primary Examiner* — James Phan
(74) *Attorney, Agent, or Firm* — NSIP Law (57) ABSTRACT

A laser operation device includes an elongated catheter, a light irradiator configured to irradiate a laser in front of a tip of the catheter, a lens disposed at a front of the light irradiator and allowing the laser to pass therethrough, a wire configured to steering the lens by pulling one side of the lens, and an elastic body configured to give an elastic force to restore the lens against a tension of the wire, wherein when the lens is steered, the laser passes through the lens and is refracted.

7 Claims, 7 Drawing Sheets

LASER OPERATION DEVICE CAPABLE OF STEERING THE LASER USING A LENS

CROSS-REFERENCE TO RELATED APPLICATION

This application claims priority to Korean Patent Application No. 10-2016-0141204, filed on Oct. 27, 2016, and all the benefits accruing therefrom under 35 U.S.C. §119, the contents of which in its entirety are herein incorporated by reference.

BACKGROUND

1. Field

The present disclosure relates to a laser operation device, and more particularly, to an insertion-type laser operation device capable of adjusting an irradiation direction of laser by using a lens.

2. Description of the Related Art

In order to minimize sequel of surgical operation of a patient, in a surgical operation such as discectomy, a minimally invasive surgery in which a thin and long catheter is inserted into a human body is widely used.

In the discectomy, a catheter is generally inserted through the tail bone or the side of a human.

In order to remove a disc, a drug may be injected through a catheter, which however does not ensure an instant and precise effect, and thus a disc has been removed using a laser from the past.

Generally, the surgery in which a catheter is inserted through the tail bone and a disc is removed using a laser is called SELD (Sacrum Epiduroscopic Laser Decompression) surgery, and the surgery in which a catheter is inserted through the side of a human and a disc is removed using a laser is called TELA (Transforaminal Epiduroscopic Laser Annuloplasty) surgery.

A device for discectomy using a laser is configured so that an optical fiber for transmitting a laser beam is inserted into an elongated catheter which may be inserted into a narrow space in a human body, so that the laser is irradiated to a target through a tip of the catheter.

During the discectomy process, if an irradiation direction of laser is not in agreement with a location of a target, the irradiation direction of laser should be changed.

In the SELD surgery, the catheter is made of a flexible and bendable material, and thus generally a laser is steered by refracting a tip of the catheter or the optical fiber. However, it is difficult to control a direction of the tip, and an excessive refraction may damage the optical fiber and cause tissue damage or pain to a patient.

In the TELA surgery, the catheter is made of hard SUS, and thus in order to steer a laser, the optical fiber should be exchanged with another optical fiber having a different irradiation direction of laser beam, which is very inconvenient.

SUMMARY

The present disclosure is directed to providing a laser operation device capable of steering a laser without controlling a direction of a tip of a catheter or exchanging a laser irradiation tool.

In one aspect of the present disclosure, there is provided a laser operation device, comprising: an elongated catheter; a light irradiator configured to irradiate a laser in front of a tip of the catheter; a lens disposed at a front of the light irradiator and allowing the laser to pass therethrough; a wire configured to steering the lens by pulling one side of the lens; and an elastic body configured to give an elastic force to restore the lens to an original location against a tension of the wire, wherein when the lens is steered, the laser passes through the lens and is refracted.

According to an embodiment, the lens may be a planoconvex lens having a convex portion disposed toward the tip of the catheter or in a direction opposite to the tip of the catheter, and a focus where the laser is concentrated may be formed at a front of the lens.

According to an embodiment, the lens may be a convex lens having at least one convex surface, and when the lens is steered, an irradiation direction of the laser may be successively changed.

According to an embodiment, the laser operation device may further comprise an adaptor inserted into the tip of the catheter, the elastic body may be a coil spring accommodated in the adaptor to surround the catheter, the lens may be attached to a front end of the coil spring, and the wire may be connected to the front end of the coil spring.

According to an embodiment, the adaptor may be formed not to bend due to the tension of the wire, and when the wire is pulled, one side of the coil spring connected to the wire may be shrunken in a length direction of the adaptor so that the lens rotates with respect to the adaptor.

According to an embodiment, the other side of the coil spring not connected to the wire may be adhered to an inner surface of the adaptor.

According to an embodiment, the wire may extend at a rear of the catheter, wind the front end of the coil spring and then extend at a rear of the catheter again, and grooves capable of accommodating the wire may be formed in a length direction at an outer surface of the catheter and an inner surface of the adaptor.

DETAILED DESCRIPTION

Hereinafter, an embodiment of the present disclosure will be described with reference to the drawings. Even though the present disclosure is described based on the embodiment depicted in the drawings, this is just an example, and the essential configuration and operations of the present disclosure are not limited thereto.

Figure 1:
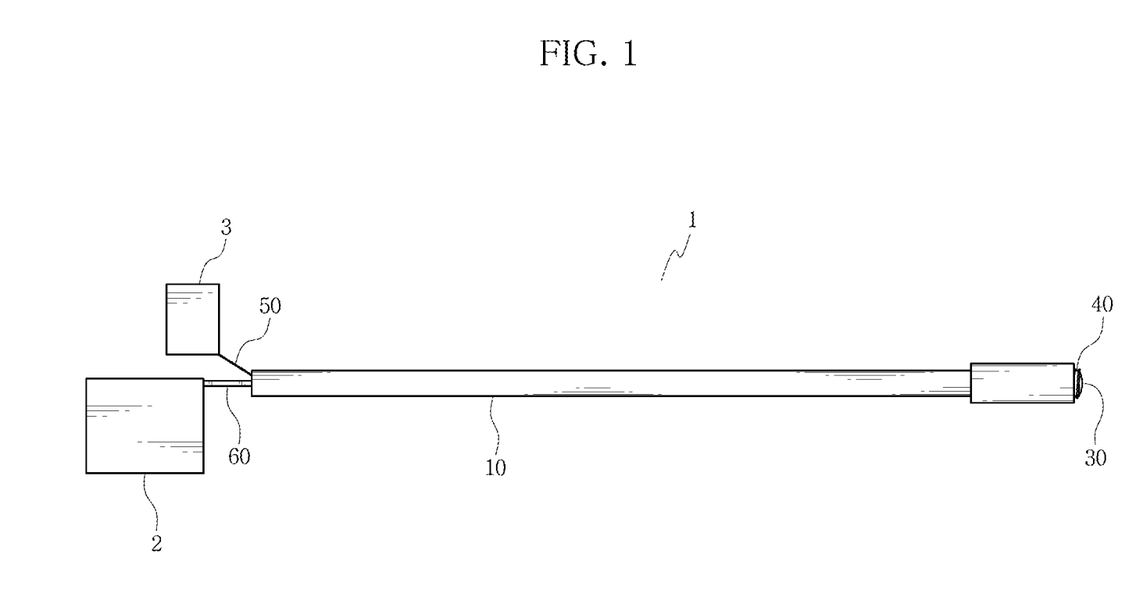
FIGS. 1 and 2 are diagrams showing a laser operation device according to an embodiment of the present disclosure.
Figure 2:
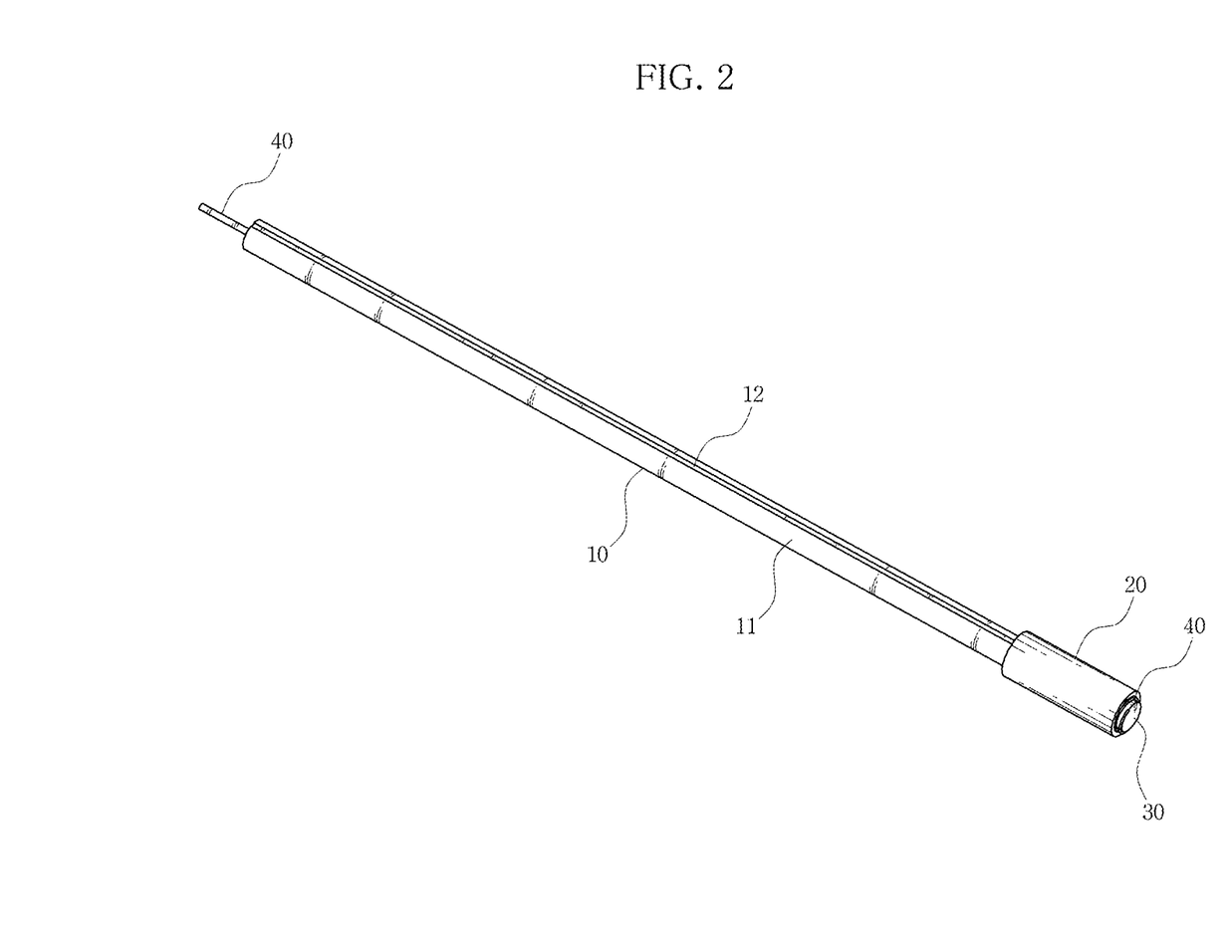

FIGS. 1 and 2 are diagrams showing a laser operation device 1 according to an embodiment of the present disclosure.

A laser operation device 1 according to this embodiment is a device which is inserted into a living body and irradiates a laser to a target (for example, a disc) to perform a surgical operation.

As shown in FIGS. 1 and 2, the laser operation device 1 includes an elongated catheter 10, an adaptor 20 inserted into a tip of the catheter 10, a light irradiator 60 inserted into the catheter 10 in a length direction, and a lens 30 disposed at a front of the light irradiator 60.

In addition, the laser operation device 1 includes a wire 50 for steering the lens 30 by pulling one side of the lens 30, and an elastic body 40 for giving an elastic force to restore the lens 30 to an original location against a tension of the wire 50.

In this embodiment, an optical fiber is used as the light irradiator 60, and a laser L irradiated from a laser source 2 connected to a rear end of the optical fiber is transferred through the inside of the optical fiber and irradiated to a front of the tip of the catheter 10.

Figure 3:
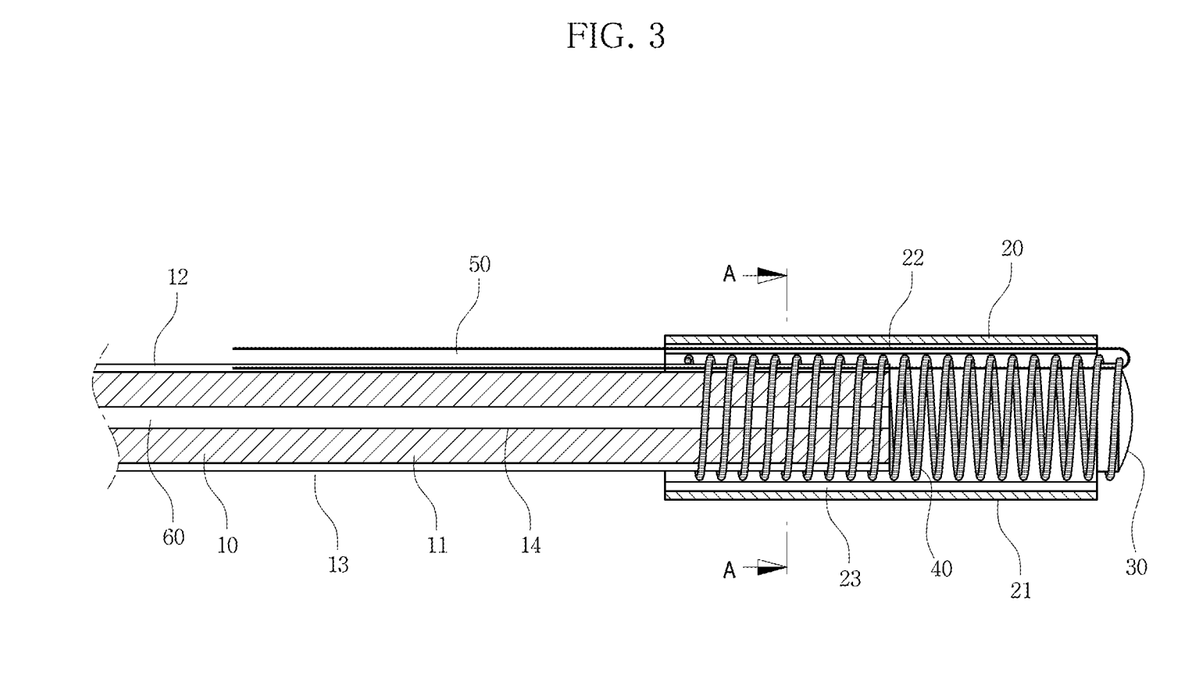
FIG. 3 is a diagram at which a front portion of the laser operation device of FIG. 1 is partially sectioned.
Figure 4:
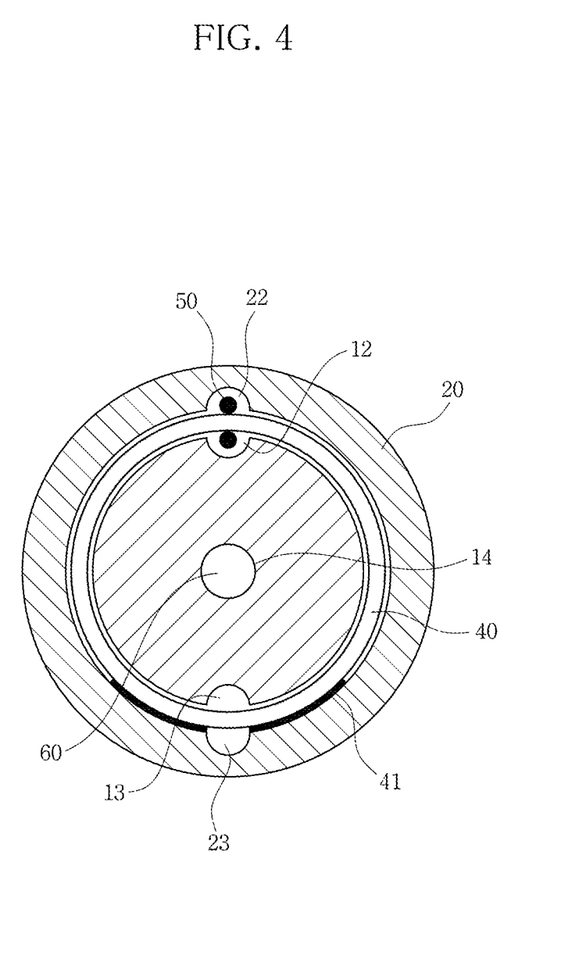
FIG. 4 is a cross-sectional view, taken along the line A-A of FIG. 3.

FIG. 3 is a diagram at which a front portion of the laser operation device 1 of FIG. 1 is partially sectioned, and FIG. 4 is a cross-sectional view, taken along the line A-A of FIG. 3.

As shown in FIG. 3, the catheter 10 has a through hole 14 formed in a length direction at a center of the body 11, and the light irradiator 60 is inserted into the through hole 14 and extends to the front tip of the catheter 10.

Hemispherical grooves 12, 13 are formed at upper and lower portions of the body 11 of the cylindrical catheter 10 in a length direction of the catheter 10. The hemispherical grooves 12, 13 play a role of a guide groove for allowing the wire 50 to extend.

Even though FIG. 2 depicts that the hemispherical groove 12 is exposed out from a rear portion of the adaptor 20, a sheath may also be formed around the catheter 10 so that the wire 50 is accurately positioned and protected.

If a single wire 50 is used for steering the lens 30 as in this embodiment, it is not needed to form the grooves 12, 13 at both upper and lower portions, and the groove may also be formed only at a region where the wire 50 passes.

An adaptor 20 having a cylindrical body 21 is interposed in the tip of the catheter 10.

Hemispherical grooves 22, 23 are formed at an inner surface of the adaptor 20 in a length direction, corresponding to the grooves 12, 13 of the catheter 10.

As well shown in FIG. 4, the groove 12 of the catheter 10 and the groove 22 of the adaptor 20 are disposed to face each other, thereby forming a path through which the wire 50 may reciprocate, and also preventing the wire 50 from deviating from an accurate location in the adaptor 20.

The elastic body 40 according to this embodiment is a coil spring. The coil spring 40 is disposed between the catheter 10 and the adaptor 20.

As shown in FIG. 3, the coil spring 40 is accommodated in the adaptor 20 to surround an outer surface of the catheter 10.

The lens 30 is attached to a front end of the coil spring 40 by means of an adhesive or the like.

The wire 50 is connected to the front end of the coil spring 40. As shown in FIGS. 3 and 4, the wire 50 extends from a rear of the catheter 10, winds the front end of the coil spring 40 and then extends to a rear of the catheter 10 again. Accordingly, the wire 50 may be coupled to the coil spring 40 without using an adhesive or any other fixture means.

In this embodiment, the lens 30 at an initial location may be steered by pulling the wire 50 rearwards. The wire 50 may be pulled using a servo motor 3 (see FIG. 1), but the wire 50 may also be manually pulled by a user, without being limited to the above.

Figure 5:
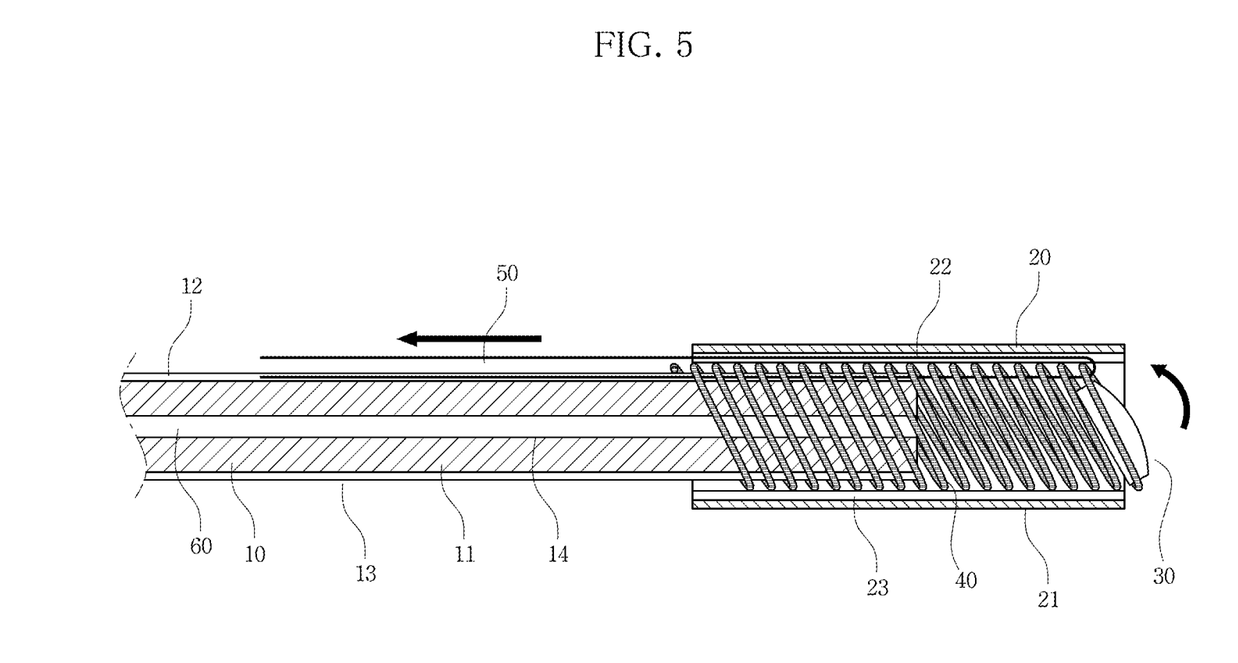
FIG. 5 is a diagram showing that a lens of the laser operation device of FIG. 3 is steered.

FIG. 5 is a diagram showing that the lens 30 is steered by means of the wire 50.

As shown in FIG. 5, if the wire 50 is pulled rearwards, the coil spring 40 connected to the wire 50 is pulled. At this time, since the wire 50 is connected to one side of the coil spring 40, one side of the coil spring 40 to which a force is applied by the wire 50 is compressed more densely in comparison to the other side of the coil spring 40 to which the wire 50 is not connected.

In this embodiment, the adaptor 20 is formed to have strength so as not to be bent by the tension of the wire 50.

Therefore, when the wire 50 pulls the coil spring 40, the adaptor 20 prevents the coil spring 40 from being bent, and one side of the coil spring 40 is shrunken in a length direction of the adaptor 20.

Since one side of the coil spring 40 is shrunken due to the force of the wire 50 and the other side of the coil spring 40 is not shrunken, the lens 30 coupled to the front end of the coil spring 40 substantially makes a pivotal movement in place.

In this configuration, even though a pivot axis is not separately formed, a pivotal movement may be obtained, and thus the configuration of the device may be simplified. In addition, when the lens 30 is steered, the coil spring 40 is not bent due to the adaptor 20, and thus it is possible to prevent an arrangement of the lens 30 and the light irradiator 60 from being distorted.

An elastic force of the compressed coil spring 40 obtained by pivoting and steering the lens 30 at a front location is applied in a direction opposite to the tension of the wire 50.

Therefore, if the force of pulling the wire 50 is released, the lens 30 is restored to an original location to face forwards by means of the elastic force of the coil spring 40.

It is also possible that two wires 50 are connected to both sides of the coil spring 40 one by one, and tensions of both wires are adjusted differently so that the lens 30 is steered in both directions.

However, when the wire 50 connected to one side of the coil spring 40 is pulled, the other side of the coil spring 40 may also be compressed together, even though the compression is not so great. In this embodiment, the wire 50 is connected to only one side of the coil spring 40, and an adhesive 41 is applied to the other side of the coil spring 40 to which the wire 50 is not connected, so that the other side of the coil spring 40 is adhered to the inner surface of the adaptor 20 (see FIG. 4).

Accordingly, it is possible to prevent the other side of the coil spring 40 to which the wire 50 is not connected from be compressed, and it is possible to ensure only one side of the coil spring 4 to which the wire 50 is compressed to be compressed, thereby accurately steering the lens 30.

Even though only a single wire 50 is provided, it is possible to steer the lens 30 in all directions by rotating the catheter 10 based on an axis in a length direction.

In this embodiment, the lens 30 is disposed at a front of the light irradiator 60 so that a laser irradiated by the light irradiator 60 passes through the lens 30. At this time, if the lens 30 is steered using the above configuration, the laser L is refracted while passing through the lens 30.

Figure 6:
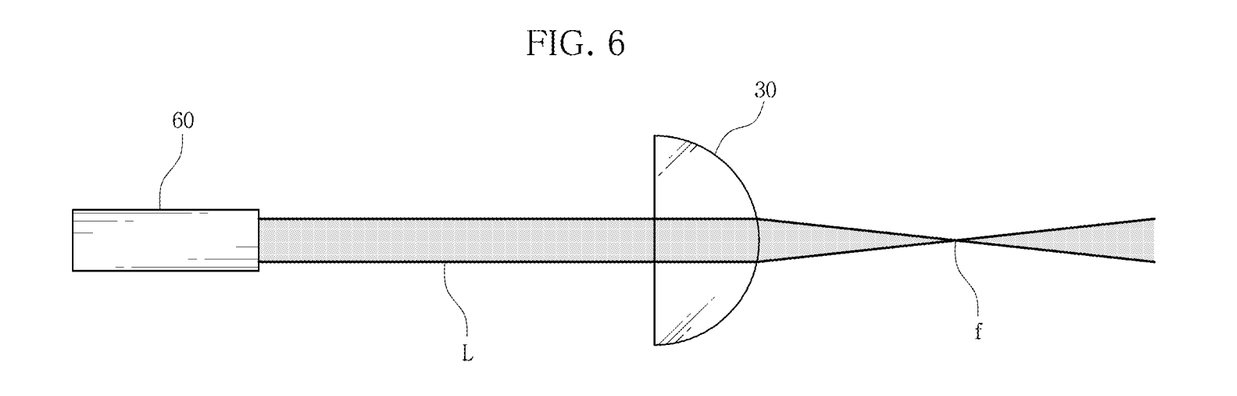
FIGS. 6 and 7 are diagrams showing that a direction of the laser is refracted using a lens of the laser operation device of FIG. 3.
Figure 7:
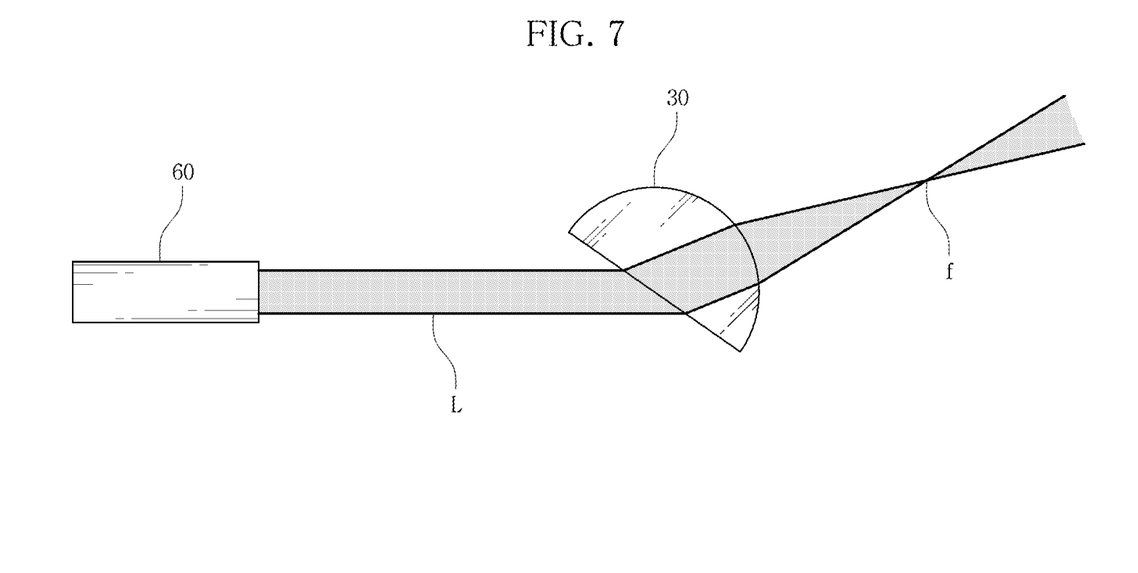

FIGS. 6 and 7 are diagrams showing that a direction of the laser L is refracted using the lens 30.

In this embodiment, the lens 30 is a convex lens having at least one convex surface, more desirably a plano-convex lens having one flat surface and one convex surface.

As shown in FIG. 6, in this embodiment, the lens 30 is disposed to have a convex portion in a direction opposite to the tip of the catheter 10.

If the plano-convex lens is used, a refraction angle of laser increases in comparison to a convex lens having two convex surfaces.

If the plano-convex lens is used, the laser L irradiated by the light irradiator 60 may be concentrated at a focus (f) at the front of the lens 30.

Therefore, by moving the focus closer to a surgical operation target, laser treatment may be performed more densely. In addition, if it is needed to irradiate a laser in a broader area rather than a density of laser, an operation device may retreat slightly from a target location to enlarge a laser irradiation area.

As shown in FIG. 7, if the lens 30 is steered, the laser L is refracted corresponding to the steering direction.

If the lens 30 is steered, an irradiation direction of the laser is changed according to the steering direction of the lens 30, and thus the irradiation direction of the laser may be successively changed by steering the lens 30, different from other optical devices such as a prism. Therefore, a surgical operation or treatment may be performed over a broad area.

Figure 8:
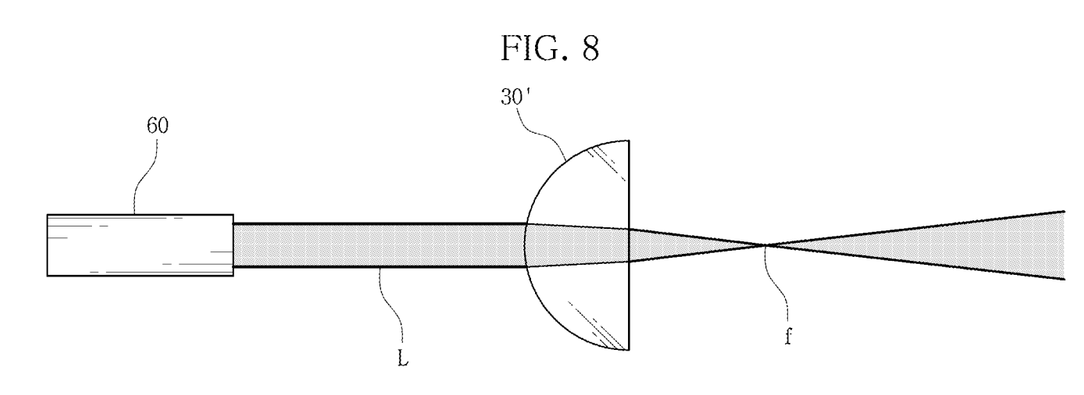
FIGS. 8 and 9 are diagrams for illustrating a laser operation device according to another embodiment of the present disclosure.
Figure 9:
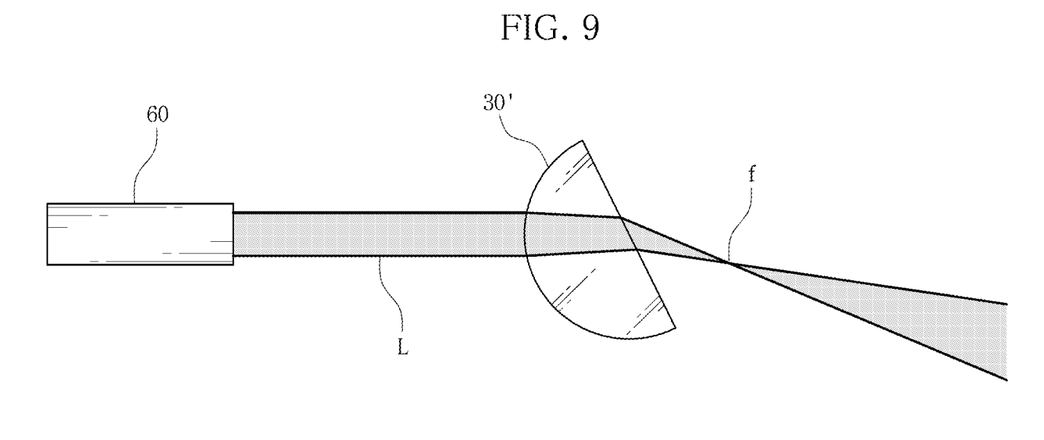

FIGS. 8 and 9 are diagrams for illustrating a laser operation device according to another embodiment of the present disclosure.

Different from the above embodiment, in this embodiment, a plano-convex lens 30' is disposed toward the tip of the catheter 10. Other configurations than the disposition of the plano-convex lens are identical to those of the former embodiment and thus not described in detail.

In this embodiment, as shown in FIG. 9, a laser L is refracted in a direction opposite to a steering direction of the lens 30'.

In this embodiment, a focus distance is relatively shortened, and a refraction index relatively increases, in comparison to the former embodiment. Therefore, if the laser operation device 1 may be positioned more closely to a target location, and a laser operation or treatment may be performed for a broader area.

According to the embodiments of the present disclosure, a laser may be steered without any complicated mechanism.

In addition, since the adaptor 20 is inserted, a laser steering mechanism may be formed in a simple way by inserting the adaptor 20 into a front portion of an existing catheter in which an optical fiber is included.

What is claimed is:
1. A laser operation device, comprising:
an elongated catheter;
a light irradiator configured to irradiate a laser in front of a tip of the catheter;
a lens disposed at a front of the light irradiator and allowing the laser to pass therethrough;
a wire configured to steering the lens by pulling one side of the lens; and
an elastic body configured to give an elastic force to restore the lens to an original location against a tension of the wire,
wherein when the lens is steered, the laser passes through the lens and is refracted.
2. The laser operation device according to claim 1,
wherein the lens is a plano-convex lens having a convex portion disposed toward the tip of the catheter or in a direction opposite to the tip of the catheter, and
wherein a focus where the laser is concentrated is formed at a front of the lens.
3. The laser operation device according to claim 1,
wherein the lens is a convex lens having at least one convex surface, and
wherein when the lens is steered, an irradiation direction of the laser is successively changed.
4. The laser operation device according to claim 1, further comprising an adaptor inserted into the tip of the catheter,
wherein the elastic body is a coil spring accommodated in the adaptor to surround the catheter, and
wherein the lens is attached to a front end of the coil spring, and the wire is connected to the front end of the coil spring.
5. The laser operation device according to claim 4,
wherein the adaptor is formed not to bend due to the tension of the wire, and
wherein when the wire is pulled, one side of the coil spring connected to the wire is shrunken in a length direction of the adaptor so that the lens rotates with respect to the adaptor.
6. The laser operation device according to claim 5,
wherein the other side of the coil spring not connected to the wire is adhered to an inner surface of the adaptor.
7. The laser operation device according to claim 4,
wherein the wire extends at a rear of the catheter, winds the front end of the coil spring and then extends at a rear of the catheter again, and
wherein grooves capable of accommodating the wire are formed in a length direction at an outer surface of the catheter and an inner surface of the adaptor.

* * * * *